United States Patent [19]

Merger et al.

[11] Patent Number: 4,851,565

[45] Date of Patent: Jul. 25, 1989

[54] CATALYZED PROCESS FOR THE PREPARATION OF AN ALIPHATIC, CYCLOALIPHATIC, ARYLALIPHATIC OR ALIPHATIC-CYCLOALIPHATIC DI- OR POLYURETHANE

[75] Inventors: Franz Merger, Frankenthal; Freidrich Towae, Ludwigshafen, both of Fed. Rep. of Germany

[73] Assignee: BASF Aktiengesellschaft, Ludwigshafen, Fed. Rep. of Germany

[21] Appl. No.: 164,860

[22] Filed: Mar. 7, 1988

Related U.S. Application Data

[63] Continuation-in-part of Ser. No. 124,701, Nov. 24, 1987, abandoned, which is a continuation-in-part of Ser. No. 135,247, Mar. 31, 1980, abandoned, and Ser. No. 879,025, Jun. 26, 1986, Pat. No. 4,713,476.

[51] Int. Cl.$^4$ ............................ C07C 125/073
[52] U.S. Cl. ........................ 560/115; 560/25; 560/158
[58] Field of Search ................... 560/115, 158, 25

[56] References Cited

U.S. PATENT DOCUMENTS

| | | | |
|---|---|---|---|
| 2,181,663 | 11/1939 | Martin | 260/2 |
| 2,409,712 | 10/1946 | Schweitzer | 260/453 |
| 2,568,885 | 9/1951 | Dreyfus | 260/77.5 |
| 2,623,867 | 12/1952 | Dreyfus | 260/77.5 |
| 2,653,144 | 9/1953 | Wielicki | 260/77.5 |
| 2,806,051 | 9/1957 | Brockway | 260/471 |
| 2,828,291 | 3/1958 | Saunders | 260/77.5 |
| 2,973,342 | 2/1961 | Inaba et al. | 260/77.5 |
| 3,046,254 | 7/1962 | Imaba et al. | 260/77.5 |
| 3,054,777 | 9/1962 | Imaba et al. | 260/77.5 |
| 3,054,819 | 9/1962 | Barclay, Jr. et al. | 260/453 |
| 3,119,793 | 1/1964 | Imaba et al. | 260/77.5 |
| 3,185,656 | 5/1965 | Gabler et al. | 260/30.2 |
| 3,223,682 | 12/1965 | Gablet et al. | 260/77.5 |
| 3,291,763 | 12/1966 | Becalick et al. | 260/13 |
| 3,366,662 | 1/1968 | Kober et al. | 260/453 |
| 3,388,103 | 6/1968 | Imohl et al. | 260/77.5 |
| 3,390,137 | 6/1968 | Kirshenbaum et al. | 260/77.5 |
| 3,412,072 | 11/1968 | Bouboulis et al. | 260/77.5 |
| 3,461,149 | 8/1969 | Hardy et al. | 260/453 |
| 3,467,687 | 9/1969 | Hardy et al. | 260/453 |
| 3,467,688 | 9/1969 | Bennett et al. | 260/453 |
| 3,481,967 | 12/1969 | Ottmann et al. | 260/453 |
| 3,523,962 | 8/1970 | Ottmann et al. | 260/453 |
| 3,574,711 | 4/1971 | Robeson | 560/157 |
| 3,734,941 | 5/1973 | Sydor | 260/453 |
| 3,763,217 | 10/1973 | Brill | 260/471 |
| 3,895,054 | 7/1975 | Zajacek et al. | 260/471 |
| 3,992,430 | 11/1976 | Bacskai | 260/453 |
| 4,081,472 | 3/1978 | Tsumura | 260/453 |
| 4,153,624 | 5/1979 | Fern | 260/453 |
| 4,388,238 | 6/1983 | Heitkamper et al. | 260/239 |
| 4,430,505 | 2/1984 | Heitkamper et al. | 560/24 |
| 4,611,079 | 9/1986 | Merger | 560/25 |

FOREIGN PATENT DOCUMENTS

| | | |
|---|---|---|
| 896412 | 7/1949 | Fed. Rep. of Germany . |
| 528437 | 5/1938 | United Kingdom . |
| 530267 | 6/1938 | United Kingdom . |
| 1025436 | 8/1964 | United Kingdom . |

OTHER PUBLICATIONS

Sandler, "Organic Functional Group Preparation," vol. II, pp. 235–239 and 244–245 (1971).
*Preparative Methods of Polymer Chemistry*, Sorenson, Interscience, 1961, pp. 92–97.
Organic Functional Group Preparation, vol. II., Sandler, pp. 135–137, 143.

*Primary Examiner*—Michael L. Shippen
*Attorney, Agent, or Firm*—William G. Conger

[57] ABSTRACT

Catalyzed processes for the preparation of aliphatic di- and polyurethanes from aliphatic di- or polyamines, urea, and monofunctional, aliphatic alcohols are disclosed which result in shorter reaction times and/or higher yields than the corresponding uncatalyzed reactions.

20 Claims, No Drawings

CATALYZED PROCESS FOR THE PREPARATION OF AN ALIPHATIC, CYCLOALIPHATIC, ARYLALIPHATIC OR ALIPHATIC-CYCLOALIPHATIC DI- OR POLYURETHANE

This is a continuation-in-part of U.S. Application Ser. No. 124,701 filed Nov. 24, 1987, now abandoned, which is a continuation in part of Ser. No. 135,247, filed Mar. 31, 1980, now abandoned, and Ser. No. 879,025 filed June 26, 1986, now U.S. Pat. No. 4,713,476 both applications claiming priority to Federal Republic of Germany application No. 2917493, filed Apr. 30, 1979, which are herein expressly incorporated by reference.

BACKGROUND OF THE INVENTION

1. Field of the Invention

The invention pertains to the preparation of an aliphatic, cycloaliphatic, arylaliphatic or aliphatic-cycloaliphatic di- or polyurethane from a primary aliphatic, cycloaliphatic, arylaliphatic or aliphatic-cycloaliphatic di- or polyamine, urea and an alcohol.

2. Description of the Prior Art

On an industrial scale, N-substituted urethanes are normally produced by the reaction of alcohols with isocyanates or by the reaction of amines with chlorocarbonates. The isocyanates and chlorocarbonates used in these reactions are obtained by phosgenation of the corresponding amines or the corresponding alcohols, respectively. HoubenWeyl, *Methods of Organic Chemistry*, Vol. 8, pages 137, 120 and 101, (George Thieme Publishers, Stuttgart, 1952). These processes are very expensive and phosgene must be used with care because of its potential danger to man and the environment.

N-substituted urethanes are used as intermediates and end products. For instance, German Published Application No. 26 35 490 and U.S. Pat. No. 3,919,278 disclose the use of N-substituted urethanes for the manufacture of isocyanates. Because of their utility, many attempts have been made to develop better methods for preparing N-substituted urethanes. These methods and their shortcomings will be discussed.

German Published Application No. 21 60 111 describes a process for the manufacture of N-substituted urethanes by reacting an organic carbonate with a primary or secondary amine in the presence of a Lewis acid. There are several problems with this process. The conversion rates are rather low and the reaction times are long. Furthermore, N-alkylarylamines are always produced as by-products. Furthermore, the organic carbonate starting materials are themselves prepared from phosgene, and thus this process does not achieve the goal of phosphene-free urethane preparation.

R. A. Franz et al, *Journal of Organic Chemistry*, Vol. 28, page 585 (1963) describe a process for making methyl-N-phenyl urethane from carbon monoxide, sulfur, aniline, and methanol. Very low yields are produced by this method; the yield does not exceed 25 percent even when there is a long reaction period.

U.S. Pat. No. 2,409,712 discloses a process for preparing monoisocyanates by the pyrolysis of N-substituted monourethanes. A process for preparing the N-alkyl and N-aryl monourethane precursors by the reaction of monoamines with urea and alcohol at temperatures of 150° C. to 350° C. under increased pressure is disclosed. However, the disclosure only describes the manufacture of N-alkylmonourethanes and does not suggest the manufacture of N,N'-disubstituted diurethanes and poly-N-polysubstituted polyurethanes. The patent further discloses that the process is not suitable for all N-substituted urethanes. Furthermore, the yields are quite low and certainly unacceptable for commercial application.

U.S. Pat. No. 2,677,698 also describes a process for the manufacture of N-substituted monurethanes. In this process, the urea is initially converted into the corresponding N,N'-disubstituted urea by reacting urea with a monoamine. The N,N'-disubstituted urea is then purified, and reacted with an alcohol. The processes described are expensive and the yields are very low. Attempts to improve the yield by improving the methods of preparing and purifying the N,N'-disubstituted ureas have not been successful.

Other processes have not been successful in eliminating the problems described thus far. For example, a process similar to that described in U.S. Pat. No. 2,409,712 is disclosed in U.S. Pat. No. 2,806,051. In this process, N-substituted monourethanes are produced by reacting alkyl or aryl monoamines with urea and alcohol at a mole ratio of 1.0:1.2:2.0 at temperatures of from 120° C. to 175° C., preferably from 125° C. to 160° C. Even within the most preferred temperature range, this process produces only low yields of N-substituted monourethanes if the reaction time is limited to a period which is practical in an industrial setting.

The processes of U.S. Pat. Nos. 2,409,712 and 2,806,051 preferably take place below 160° C. The reason for this preference for low temperatures is presumably the tendency for urea and substituted ureas to react to form biurets and other products at higher temperatures. For example, urea is known to condense to form biuret and cyanuric acid at temperatures of from 150° C. to 175° C. Erickson, in *J. Am. Chem. Soc.* 76, 3977–78, showed that alkyl amines react with urea at lower temperatures, i.e. 160° C. to 165° C., to produce mono- and di-substituted ureas while at a higher temperature of 170° C. to 200° C., monosubstituted and 1,3-disubstituted biurets were formed. For these and other reasons, the use of higher temperatures in reactions involving urea, and especially urea and amines, has been avoided.

In view of the problems disclosed in U.S. Pat. Nos. 2,409,712 and 2,806,051 with respect to yields and reaction times, it is no wonder that further attempts to produce N-alkylurethanes have not involved the reaction between amines, urea, and alcohol. The inventors of U.S. Pat. No. 3,076,007, for example, in searching for a commercially viable, non-phosgene approach to N-substituted monourethanes describe the N-alkyl, N-alkoxyalkyl and N-alkoxyalkoxyalkyl monourethanes of U.S. Pat. No. 2,409,712 as requiring phosgene for their preparation due to the fact that the available non-phosgene methods reduce poor yields with numerous side reactions.

It is thus surprising that aliphatic, cycloaliphatic, arylaliphatic, and aliphatic-cycloaliphatic N-substituted di- and polyurethanes can be produced in a single process with good yields by reacting a diamine with urea and alcohol at higher temperatures, preferably temperatures of from greater than 170° C. to 250° C., and most preferably from 170° C. to 230° C. Prior teachings indicate that diureas and polyureas are obtained from diamines and urea; for example, hexamethylenediurea is obtained from hexamethylenediamine and urea. The prior art also teaches that, although urea and alcohol may react to produce O-carbamates, they continue to react to form N,N'-disubstituted ureas in the presence of amines. See Houben-Weyl, *Methods of Organic Chemistry*, Vol. 8, pages 151 and 140, (George Thieme Publishers, Stuttgart, 1952). These side reactions decrease the yield of the desired product.

None of the references cited discloses the preparation of aliphatic, cycloaliphatic, arylaliphatic or aliphatic-cycloaliphatic N-substituted di- and polyurethanes by reacting diamines or polyamines with urea and alcohol. Neither do the references disclose the unexpectedly high yields obtainable at higher temperatures. The reaction temperatures utilized in U.S. Pat. No. 2,806,051, for example, are low and only monoamines are used in this process. If diamines are used under these process conditions, one obtains high yields of a polymeric precipitate with a polyurea structure similar to the polyureas which are formed from diamines and polyisocyanates.

The use of higher temperatures for the reaction between diamines, urea, and alcohol is neither taught nor suggested in the prior art. As a matter of fact, the prior art suggests that higher temperatures should be avoided, as the patent and non-patent literature is replete with examples wherein diamines and urea participate in numerous reactions at higher temperatures yielding substituted biurets or a variety of other by-products; or participate in condensation reactions at higher temperatures to form polyurea thermoplastics.

For example, German Pat. No. 896,412 indicates that high molecular weight, spinnable condensation products may be produced from the reaction of diamines with urea or other diamides of carbonic acid. This result is likely to occur if the amino groups of the diamines are separated by a chain of more than three atoms. Preparation of polyureas is taught in many other references also. In Great Britain Pat. No. 530,267, for example, urea reacts with aliphatic diamines in the presence of aromatic alcohols such as phenol and m-cresol at temperatures of from 100° C. to 270° C. High molecular weight polyureas are the product of this reaction. In U.S. Pat. No. 2,973,342, urea and diamines are reacted in the presence of water to form spinnable polyurea condensates at temperatures of from 130° C. to 200° C. U.S. Pat. No. 3,412,072 discloses the preparation of polyurea themoplastics by reacting diamines with urea in the presence of aliphatic alcohols such as ethanol and isopropanol at temperatures from 90° C. to 300° C.

In addition to the expected reaction of diamines with urea to form polyureas, any diurethanes formed may further react with unreacted diamine to form polyureas. For example, U.S. Pat. Nos. 2,181,663 and 2,568,885 disclose that high molecular weight polyureas with molecular weights of 8000 to 10,000 and greater, may be produced when diurethanes are condensed with diamines at temperatures of approximately 150° C. to 300° C. Moreover, as mono-, di-, and polyurethanes can be split thermally into isocyanates, alcohols, olefins, carbon dioxide, ureas, and carbodiimides, these products can further react to form numerous by-products such as biurets, allophanates, isocyanurates, and polycarbodiimides, among others. See *The Journal of the American Chemical Society*, Vol. 80, page 5495 (1958) and Vol. 48, page 1946 (1956).

In view of the problems disclosed in the prior art and the many possible side reactions, particularly polyurea formation, it was surprising that the process of the subject invention, which involves similar reaction conditions, would result in N-substituted di- and polyurethanes with excellent yields and in exceptional purity.

SUMMARY OF THE INVENTION

The object of the invention is to produce an aliphatic, cycloaliphatic, arylaliphatic, or aliphatic-cycloaliphatic di- or polyurethane from readily available raw materials, with acceptable yields, and under economically justifiable conditions. The use of strongly toxic raw materials such as phosgene and carbon monoxide, or raw materials which themselves require the use of phosgene for their preparation, is to be avoided. These and other objects were unexpectedly met through the use of a catalytic process for the preparation of aliphatic, cycloaliphatic, arylaliphatic and aliphatic-cycloaliphatic di- and polyurethanes comprising the steps of:

A. reacting in the presence of a catalyst which accelerates the formation of N-substituted, N-carbanates, a primary aliphatic, cycloaliphatic, arylaliphatic, or aliphatic-cycloaliphatic di- or polyamine with urea and a monofunctional, aliphatic, cycloaliphatic, arylaliphatic, or aliphatic-cycloaliphatic alcohol at temperatures of from about 170° C. to 250° C., B. separating the aliphatic, cycloaliphatic, arylaliphatic, or aliphatic-cycloaliphatic di- or polyurethane from the ammonia and other by-products thus produced.

The reaction may be illustrated by the following equation:

The aliphatic, cycloaliphatic, arylaliphatic, or aliphatic-cycloaliphatic di- or polyurethanes produced according to the process of this invention are valuable end and intermediate products. They may be utilized, for instance, as pesticides. As intermediate products, they are useful as components are for polycondensation and polymer systems and, in particular, they are transformed into the corresponding di- or polyisocyanates by thermal cleavage and removal of the alcohol thermolysis product. The di- and polyisocyanates can be used in the manufacture of polyurethanes.

DESCRIPTION OF THE PREFERRED EMBODIMENTS

In order to prepare the aliphatic, cycloaliphatic, arylaliphatic, or aliphatic-cycloaliphatic di- and polyurethanes in accordance with the process of this invention, a primary aliphatic, cycloaliphatic, arylaliphatic or aliphatic-cycloaliphatic di- or polyamine and a monofunctional aliphatic alcohol are reacted with the urea in such quantities that the ratio of amino groups of the amine to urea to hydroxyl groups of the alcohol is 1:0.7-10:1-50, preferably 1:0.9-2.5:1.25-15 and in particular, 1:1-2:1.25-10.

The reaction preferably is carried out in the presence of excess alcohol at temperatures of from 170° C. to 250° C. under suitable pressure. One or more catalysts are added to the reaction mixture in order to increase the reaction rate. It has prove to be advantageous to immediately remove the resultant ammonia from the reaction mixture as it is formed, for instance, by means of fractional distillation.

Amines having the formula $R-(NH_2)_n$ are well suited for the reaction with urea and alcohols according to this invention. In the formula, R represents a multifunctional, optionally substituted aliphatic or cycloaliphatic radical or mixed radical of this type; and n stands for a whole number, the value of which corresponds with the valency of R and is at least 2, preferably 2 to 5, and particularly 2. The aliphatic radicals contain 2 to 20, preferably 3 to 16, and particularly 4 to 12, carbon atoms; they may have a straight chain or a branched structure; and they may contain interspersed heteroatoms such as oxygen, sulfur or a tertiary nitrogen atom, or bivalent heterocyclic radicals as bridge members in bonded form. The cycloaliphatic radicals contain 5 to 12, preferably 6 to 12, carbon atoms whereas the mixed radicals of this type contain 8 to 50, preferably 10 to 15, carbon atoms. Representative examples include: aliphatic diamines such as ethylenediamine, 1,3- and 1,2-propanediamine, 2,2-dimethyl-1,3-propanediamine, 1,4-butanediamine, 1,5-pentamethylenediamine, 1,6-hexamethylenediamine, 2,2,4-trimethyl-1,6-hexamethylenediamine, 1,8-octamethylenediamine, 1,10-decylenediamine, and 1,12-dodecylenediamine; cycloaliphatic diamines such as 1,2-, 1,3-, and 1,4-cyclohexanediamine, 2,4- and 2,6-hexahydrotoluenediamine, as well as the corresponding isomer mixture; aliphatic-cycloaliphatic diamines such as 1,4-hexahydroxylenediamine, 4,4'-, 2,4'- and 2,2'-diamino-dicyclohexylmethane as well as the corresponding isomer mixtures, 2,2-bis(4-aminocyclohexyl)propane, 3-aminomethyl-3,5,5-trimethylcyclohexylamine; dicyclopentadienyl compounds having the formula

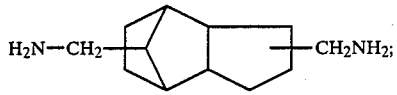

polyamines such as polycyclohexylpolymethylene polyamines having the formula

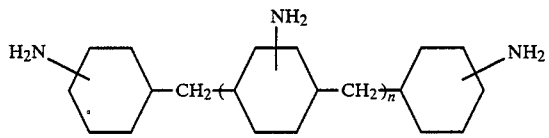

wherein n=1 to 4; and diamines containing, in bonded form, mixtures of diaminodicyclohexylmethanes and polycyclohexylpolymethylene polyamines and heteroatoms or heterocyclic radicals such as 3,3'-diaminodipropyl ether, or optionally substituted N,N'-bis(2,2-dimethyl-3-aminopropyl)piperazine and N,N'-bis-(3-aminoproply)piperazine.

Preferably used as amines are 1,6-hexamethylene diamine, 2,2,4-trimethyl-1,6-hexamethylenediamine, 1,4-hexahydroxylenediamine, 2,4- and 2,6-hexahydrotoluenediamine as well as the corresponding isomer mixtures, 4,4'-diaminodicyclohexylmethane, 1,4-diaminocyclohexane, 2,2-bis(4-aminocyclohexyl)propane and 3-aminomethyl-3,5,5-trimethylcycohexylamines.

Any desired unsubstituted or substituted primary or secondary aliphatic alcohols or aromatic-aliphatic (arylaliphatic) alcohol, as well as mixtures thereof, may be used as the monofunctional alcohol for the process according to this invention. Examples include primary aliphatic monoalcohols having 1 to 20 carbon atoms, preferably 1 to 10 carbon atoms, such as methanol, ethanol, propanol, n-butanol, isobutanol, 2- and 3-methylbutanol, neopentyl alcohol, pentanol, 2-methylpentanol, n-hexanol, 2-ethyl-hexanol, n-heptanol, n-octanol, n-nonanol, n-decanol, n-dodecanol, 2-phenyl-propanol and benzyl alcohol; and secondary aliphatic and cycloaliphatic monoalcohols having 3 to 15 carbon atoms, preferably 3 to 6 carbon atoms, such as isopropanol, sec-butanol, sec-isoamyl alcohol, cyclopentanol, cyclohexanol, 2-, 3-, or 4-methylcyclohexanol, and 4-tertiary-butylcyclohexanol. Preferably used are the monoalcohols methanol, ethanol, propanol, butanol, isobutanol, 2- and 3-methylbutanol, 2-ethylbutanol, pentanol, 2-methylpentanol, hexanol, 2-ethylhexanol, heptanol, octanol, and cyclohexanol.

As already indicated, the reaction preferably is carried out with excess alcohol so that the alcohol functions as a reaction component and simultaneously as a solvent. Instead of alcohol, however, mixtures of alcohols and other organic solvents which are inert under the reaction conditions may also be used as solvents.

According to this invention, the aliphatic, cycloaliphatic, arylaliphatic, or aliphatic-cycloaliphatic di- or polyurethane, preferably diurethane, is produced in the presence of one or more suitable catalysts. The catalyst should be present in quantities of 0.1 to 20 percent by weight, preferably 0.5 to 10 percent by weight, and in particular 1 to 5 percent by weight relative to the weight of the primary di- or polyamine. Suitable catalysts are inorganic or organic compounds containing one or more, preferably one cation of metals of the groups IA, IB, IIA, IIB, IIIA, IIIB, IVA, IVB, VA, VB, VIB, VIIB, AND VIIIB of the periodic system defined in accordance with the *Handbook of Chemistry and Physics*, (14th edition, Chemical Rubber Publishing Company, 2310 Superior Avenue N.W., Cleveland, Ohio). These compounds include, for instance, halides such as chlorides and bromides, sulfates, phosphates, nitrates, borates, alcoholates, phenolates, sulfonates, oxides, hydrated oxides, hydroxides, carboxylates, chelates, carbonates, and thio- or dithiocarbamates. The compounds may contain cations of any of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt and nickel. Preferably used are the cations of lithium, calcium, aluminum, tin, bismuth, antimony, copper, zinc, titanium, vanadium, chromium, molybdenum, manganese, iron and cobalt. Without any recognizable marked drawbacks, the catalysts may also be used in the form of their hydrates or ammoniates.

Examples of typical catalysts include the following compounds: lithium methoxide, lithium ethoxide, lithium propoxide, lithium butoxide, sodium methoxide, potassium tertiary butoxide, magnesium methoxide, calcium methoxide, tin(II) chloride, tin(IV) chloride, lead acetate, lead phosphate, antimony(III) chloride, antimony(V) chloride, aluminum isobutoxide, aluminum chloride, bismuth(III) chloride, copper(II) acetate, copper(II) sulfate, copper(II) nitrate, bis(triphenylphosphineoxide)-copper(II) chloride, copper molybdate, silver acetate, gold acetate, zinc oxide, zinc chloride, zinc acetate, zinc acetonylacetate, zinc octoate, zinc oxalate, zinc hexylate, zinc benzoate, zinc undecylenate, cerium(IV) oxide, uranyl acetate, titanium tetrabutoxide, titanium tetrachloride, titanium tetraphenolate, titanium naphthenate, vanadium(III) chloride, vanadium acetonylacetate, chromium(III) chloride, molybdenum(VI) oxide, molybdenum acetylacetonate, tungsten(VI) oxide, manganese(II) chloride, manganese(II) acetate, manganese(III) acetate, iron(II) acetate, iron(III) acetate, iron phosphate, iron oxylate, iron(III) chloride, iron(III) bromide, cobalt acetate, cobalt chloride, cobalt sulfate, cobalt naphthenate, nickel chloride, nickel acetate and nickel naphthenate as well as their mixtures.

The reaction takes place at temperatures of 170° C. to 250° C., preferably from 170° C. to 230° C., and more preferably from 185° C. to 230° C., at pressures of 0.1 bar to 120 bar, preferably 0.5 bar to 60 bar, and in particular from 1 bar to 40 bar. The reaction times, which are appropriate for these conditions, are 0.1 hour to 50 hours, preferably 1 hour to 20 hours, and particularly 4 hours to 12 hours. At a given temperature, the reaction is preferably carried out under a pressure which allows the resultant ammonia to be fractionally distilled out of the reaction mixture. The necessary parameters may be taken from tables of physical characteristic data for ammonia and alcohols.

One way of preparing the di- and polyurethanes is to mix the reactants in the corresponding mole ratios, in the presence of the selected catalyst, in a pressurized or unpressurized reaction vessel equipped with a device for separating the ammonia, and then to heat the mixture to the required temperature. The resulting ammonia can be separated after the reaction has been completed. Preferably, however, it is distilled off during the reaction. It may be advantageous, particularly in the case of the reaction of low molecular weight alcohols under pressure, to separate the ammonia by using a stripping agent which is inert under the reaction conditions, such as a gas like nitrogen.

A particularly advantageous method of preparing the di- and polyurethanes which, as a rule, results in a considerable reduction of the reaction time, is described as follows: (1) The primary aliphatic, cycloaliphatic, arylaliphatic or cycloaliphatic-aliphatic di- or polyamine, urea, and the alcohol are initially reacted in a ratio of the amino groups of the amine to urea to hydroxyl groups of the alcohol of from 1:1-1.5:1-2, preferably 1:1-1.25:1.25-1.75 for 1 hour to 4 hours, preferably 2 hours to 3 hours. (2) Subsequently, additional alcohol is added to the reaction mixture in an amount such that from 2.5 to about 7.5, preferably 3 to 6 moles of alcohol are present per $NH_2$ group of the amine and such that the reaction is completed in a total time period of 4 hours to 20 hours, preferably 5 hours to 12 hours. (3) Thereafter, before or after removing the catalyst and filtering out solid materials, the di- or polyurethanes are isolated from the resulting reaction mixture. This may be done, for instance, by completely distilling off the alcohol and any solvent as well as any O-alkyl carbamates which are formed as by-products, by partially distilling off the alcohol followed by crystallization, by crystalliation, or by precipitation with or transcrystallization from other solvents.

The parts referred to in the specific examples which follow are relative to weight. The elementary compositions and structures were confirmed by elementary analysis, mass spectrometry, as well as infra-red and nuclear magnetic resonance spectra.

EXAMPLE 1

Agitated in a reaction vessel are 116 parts of 1,6-hexamethylenediamine with 120 parts of urea and 1300 parts of n-octanol-(1) at a reflux temperature of 185° C.-200° C. at normal pressure for 20 hours while ammonia is simultaneously removed by distillation. The reaction product crystallizes upon cooling of the reaction mixture. By filtration and drying, 389 parts of 1,6-bis-(octoxycarbonylamino)-hexane, $C_{24}H_{48}N_2O_4$ (molecular weight 428), are obtained corresponding with 91 percent of theory, relative to the raw materials, 1,6-hexamethylenediamine and urea. The melting point is 108° C.-109° C.

EXAMPLE 2

In accordance with Example 1, 116 parts of 1,6-hexamethylenediamine are heated to the reflux temperature with 120 parts of urea, 1.5 parts sodium octylate, and 1300 parts of n-octanol-(1) for 16 hours. After cooling, filtration, washing with n-octanol-(1) and drying, 396 parts of 1,6-bis-(octoxycarbonylamino)hexane are obtained corresponding with 92.5 percent of theory. The melting point is 106° C.-108° C.

EXAMPLE 3

In a reaction vessel, 5.8 parts of 1,6-hexamethylenediamine are heated with 7.2 parts of urea and 9.2 parts of ethanol to 170° C. to 175° C. for 13 hours, and accompanied by a throughput of 7 liters of nitrogen per hour per liter of reaction mixture via a dip tube while a pressure of 15 bars to 16 bars is adjusted in the reactor via a pressure valve so that the reaction mixture boils. After cooling, the reaction mixture is examined gas chromatographically according to the internal standard method. This shows that the 1,6-hexamethylenediamine was essentially completely reacted with 10.9 parts (83.8) percent theory relative to reacted 1,6-hexamethylenediamine) of 1,6-bis(ethoxycarbonylamino)hexane having been produced. This corresponds with a volume-time yield of 37.8 grams per liter per hour.

EXAMPLES 4-8

The process of Example 3 was duplicated with the exception that 0.1 part of various catalysts was added to the reaction mixture.

The catalysts used, the reaction times, and the resulting yields have been summarized in the following table.

TABLE

| Example | Catalyst | Time (hours) | Yield (%) | Volume-Time-Yield (g/l/h) |
|---|---|---|---|---|
| 4 | Cobalt(II) acetate | 5.5 | 79.2 | 84.4 |
| 5 | Iron(II) acetate | 5.0 | 73.1 | 85.6 |
| 6 | Vanadium trichloride | 5.0 | 61.5 | 72.1 |
| 7 | Zinc naphthenate | 7.0 | 78.5 | 65.6 |
| 8 | Manganese(II) acetate | 7.0 | 82.4 | 68.9 |

COMPARISON EXAMPLES

Comparison examples A and B were performed to help illustrate the advantages of the subject invention over the process of U.S. Pat. No. 2,806,051. As previously discussed, one skilled in the art would expect diamines to react with urea in the presence of alcohol to produce high molecular weight polyurea thermoplastics. Comparison example A, which utilizes the reaction conditions and reactant ratios of U.S. Pat. No.

2,806,051, bears this out, yielding only polyhexamethylenepolyurea.

In Comparison Example B, the reactant conditions remain those of U.S. Pat. No. 2,806,051, but the reactant ratios were changed to correspond to those claimed in the process of the subject invention. Nevertheless, the sole product is again polyhexamethylenepolyurea.

In Comparison Example C, the raw materials and reactant ratios of subject invention Example I were followed, but a temperature near the upper end of the preferred range of U.S. Pat. No. 2,806,051 was utilized. Again, only polyhexamethylenepolyurea could be detected. These comparison examples clearly indicate that one would not expect to be able to produce di- or polyurethanes from di- or polyfunctional amines in a Brockway-type process, but should expect high molecular weight polyureas instead. Note that even when large excesses of alcohol, and when urea to amino group equivalent ratios of 2:1 are used, as in Example C, that high molecular weight polyureas are still obtained in the portion of Brockway's range which he discloses as most optimal.

COMPARISON EXAMPLE A

A reaction vessel is charged with 1.0 mole of 1,6-hexanediamine, 2.4 moles urea, and 2.0 moles n-butanol and maintained at 120° C. to 150° C. and 1 bar to 3 bars for a period of 20 hours. Considerable quantities of an amorphous solid material separate. The infrared spectrum (after filtering and drying) is virtually identical with the spectrum of poly[hexamethyleneurea). The material does not dissolve after heating in n-butanol at 190° C. and 6 bars to 7 bars for two hours. No 1,6-bis(-butoxycarbonylamino)hexane could be isolated from the filtrate of the reaction mixture.

COMPARISON EXAMPLE B

A reaction vessel is charged with 1.0 mole 1,6-hexanediamine, 2.4 moles urea, and 11.3 moles n-butanol and maintained at reflux for 50 hours. During this time the reflux temperature slowly increases from 118° C. to 145° C. Large amounts of an amorphous solid precipitated. This solid is insoluble in the usual solvents and possesses an infrared spectrum virtually identical with polyhexamethylenepolyurea. No 1,6-bis(butoxycarbonylamino)hexane is detectable in either the filter cake or the filtrate.

COMPARISON EXAMPLE C

A reaction vessel is charged with 1.0 mole 1,6-hexanediamine, 2.0 moles urea, and 10.0 moles 1-octanol as in Example 1. The pressure is adusted to maintain reflux at 150° C. over a period of 20 hours. Ammonia is removed by fractional distillation. A large quantity of an amorphous solid is separated by filtration. The infrared spectrum of this solid corresponds to that of a polyurea. No 1,6-bis(octoxycarbonylamino) hexane can be detected in either the filter cake or filtrate.

Comparison Examples A-C illustrate the differences between the prior art non-catalytic processes useful for preparing monourethanes and those same or similar processes for preparing polyurethanes. Under the conditions disclosed by the prior art as optimal, only high molecular weight polyureas are formed when polyurethane preparation is attempted. Comparison Examples D and E illustrate that the addition of a catalyst to the prior art processes makes no difference in the result.

Comparison Examples D and E repeat the catalyzed reactions of Examples 4 and 8 respectively, but the pressure is maintained at 7–10 bar, corresponding to a reaction temperature of approximately 155° C. Despite the presence of the same catalysts which had proven to be highly effective in preparing the desired diurethane product at temperatures of 170°–175° C., no diurethane is produced. Only substituted ureas and polyureas are isolated. In addition, the reaction mixture contains considerable quantities of O-ethylcarbamate.

EXAMPLE 9

Example 4 is repeated, but with a mole ratio of urea to diamine of 2.0:1 instead of 2.4:1. Essentially no O-ethylcarbamate is produced.

EXAMPLE 10

Example 4 is repeated to ascertain the presence of O-ethylcarbamate. The product mixture, in addition to the desired 1,6-bis(ethoxycarbonylamino)hexane, contains approximately 0.3 mole O-ethylcarbamate.

Examples 9 and 10 indicate that the catalysts of the subject invention are not useful in preparing O-alkylcarbamates when utilized in the presence of amines. In Example 9 where there is no excess of urea over amine, essentially no O-ethylcarbamate is formed. In Example 10, where urea is present in 0.4 molar excess, somewhat greater than approximately 0.3 mole of O-ethylcarbamate can be expected to be present in the reaction mixture. This corresponds to approximately an 80% yield based on excess urea.

Together, Examples 9 and 10 illustrate that urea and alcohol do not react to any substantial degree under the claimed reaction conditions to form O-alkylcarbamates as long as some amine-functional reactant is present. Only when the amine disappears by virtue of its conversion to the desired bis- or poly(alkoxycarbonylamino)alkane product, can any urea present in excess react with the alcohol to form O-alkylcarbamate.

The failure of the catalysts of the subject invention to catalyze the formation of O-alkylcarbamates in the presence of amines is predictable based on the differences in the nucleophilic character of alcohol and the amine. Alcohol, being a much weaker nucleophile, cannot compete with the amine in its reaction with urea until essentially all of the amine disappears from the reaction mixture. Thus the reactions disclosed by Robeson in U.S. Pat. No. 3,574,711 and Sandler in *Organic Functional Group Preparation*, Vol. II, pp. 233-245 are inapplicable to reaction mixtures which, in addition to urea and alcohol, also contain significant quantities of amines.

The embodiments of the invention in which an exclusive privilege or property is claimed are defined as follows:

1. A process for the preparation of a di- or polyurethane having the formula

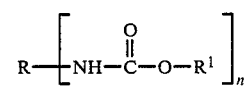

comprising:
(a) reacting at a reaction temperature of from about 170° C. to about 250° C.,
(i) a primary di- or polyamine having the formula $$R\text{---}[NH_2]_n$$

wherein R is an n-valent aliphatic, cycloaliphatic, or cycloaliphatic-aliphatic organic radical;
 (ii) urea;
 (iii) a monofunctional alcohol having the formula
$$R^1OH$$
wherein R is a monovalent aliphatic, cycloaliphatic, arylaliphatic, or cycloaliphatic-aliphatic organic radical;
 wherein the mole ratio of amino groups: urea:alcohol is from about 1:0.7:1 to about 1:10:50, in the presence of an effective amount of a catalyst containing a cation of a metal selected from the group consisting of the metals of Groups IA, IB, IIA, IIB, IIIA, IIIB, IVA, IVB, VA, VB, VIB, VIIB, and VIIIB of the periodic table of elements; and
 (b) separating the di- or polyurethane product from the reaction mixture.

2. The process of claim 1, further comprising:
 (c) continously separating ammonia produced during the course of the reaction as it is formed.

3. The process of claim 1 wherein said primary di- or polyamine is selected from the group consisting of 1,4-hexahydroxylenediamine, 2,4- and 2,6-hexahydrotoluenediamine, 4,4'-diaminodicyclohexylmethane, 1,4-diaminocyclohexane, 2,2-bis(4-aminocyclohexyl)-propane, 3-aminomethyl- 3,5,5-trimethylcyclohexylamine, 1,6-hexanediamine, 1,4-butanediamine, 1,5-pentanediamine, 1,8-octanediamine, 1,10-decanediamine, 1,12-dodecanediamine, and mixtures thereof.

4. The process of claim 2 wherein said primary di- or polyamine is selected from the group consisting of 1,4-hexahydroxylenediamine, 2,4- and 2,6-hexahydrotoluenediamine, 4,4'-diaminodicyclohexylmethane, 1,4-diaminocyclohexane, 2,2-bis(4-aminocyclohexyl)-propane, 3-aminomethyl-3,5,5-trimethylcyclohexylamine, 1,6-hexanediamine, 1,4-butanediamine, 1,5-pentanediamine, 1,8-octanediamine, 1,10-decanediamine, 1,12-dodecanediamine, and mixtures thereof.

5. The process of claim 1 wherein said alcohol is selected from the group consisting of methanol, ethanol, propanol, butanol, isobutanol, 2- and 3-methylbutanol, 2-ethylbutanol, pentanol, 2-methylpentanol, hexanol, 2-ethylhexanol, heptanol, octanol, cyclohexanol, and mixtures thereof.

6. The process of claim 2 wherein said alcohol is selected from the group consisting of methanol, ethanol, propanol, butanol, isobutanol, 2- and 3-methylbutanol, 2-ethylbutanol, pentanol, 2-methylpentanol, hexanol, 2-ethylhexanol, heptanol, octanol, cyclohexanol, and mixtures thereof.

7. The process of claim 4 wherein said alcohol is selected from the group consisting of methanol, ethanol, propanol, butanol, isobutanol, 2- and 3-methylbutanol, 2-ethylbutanol, pentanol, 2-methylpentanol, hexanol, 2-ethylhexanol, heptanol, octanol, cyclohexanol, and mixtures thereof.

8. The process of claim 2 wherein said metal cation is selected from the group consisting of the metal cations of cobalt, iron, vanadium, zinc, and manganese.

9. The process of claim 4 wherein said metal cation is selected from the group consisting of the metal cations of cobalt, iron, vanadium, zinc, and manganese.

10. The process of claim 1 wherein said alcohol reactant (ii) is added to reactants (i) and (iii) in two or more portions, the first portion being such that the amino group: urea:alcohol mole ratio is from about 1:1:1 to about 1:1.5:2 and is reacted for a period of from 1 to about 4 hours, following which additional alcohol is added such that the overall amino group: urea:alcohol mole ratio is from about 1:1:2.5 to about 1:1.5:7.5, such that the overall reaction is completed in a total time period of from about 4 hours to about 20 hours, and wherein said total time period is of shorter duration than the time period resulting from a reaction under similar conditions but where all the alcohol is added at once.

11. The process of claim 2 wherein said alcohol reactant (ii) is added to reactants (i) and (iii) in two or more portions, the first portion being such that the amino group: urea:alcohol mole ratio is from about 1:1:1 to about 1:1.5:2 and is reacted for a period of from 1 to about 4 hours, following which additional alcohol is added such that the overall amino group: urea:alcohol mole ratio is from about 1:1:2.5 to about 1:1.5:7.5, such that the overall reaction is completed in a total time period of from about 4 hours to about 20 hours, and wherein said total time period is of shorter duration than the time period resulting from a reaction under similar conditions but where all the alcohol is added at once.

12. The process of claim 4 wherein said alcohol reactant (ii) is added to reactants (i) and (iii) in two or more portions, the first portion being such that the amino group: urea:alcohol mole ratio is from about 1:1:1 to about 1:1.5:2 and is reacted for a period of from 1 to about 4 hours, following which additional alcohol is added such that the overall amino group : urea : alcohol mole ratio is from about 1:1:2.5 to about 1:1.5:7.5, such that the overall reaction is completed in a total time period of from about 4 hours to about 20 hours, and wherein said total time period is of shorter duration than the time period resulting from a reaction under similar conditions but where all the alcohol is added at once.

13. The process of claim 7 wherein said alcohol reactant (ii) is added to reactants (i) and (iii) in two or more portions, the first portion being such that the amino group: urea:alcohol mole ratio is from about 1:1:1 to about 1:1.5:2 and is reacted for a period of from 1 to about 4 hours, following which additional alcohol is added such that the overall amino group: urea:alcohol mole ratio is from about 1:1:2.5 to about 1:1.5:7.5, such that the overall reaction is completed in a total time period of from about 4 hours to about 20 hours, and wherein said total time period is of shorter duration than the time period resulting from a reaction under similar conditions but where all the alcohol is added at once.

14. The process of claim 1 wherein said reaction temperature is from 185° C.–230° C.

15. The process of claim 2 wherein said reaction temperature is from 185° C.–230° C.

16. The process of claim 4 wherein said reaction temperature is from 185° C.–230° C.

17. The process of claim 7 wherein said reaction temperature is from 185° C.–230° C.

18. The process of claim 8 wherein said reaction temperature is from 185° C.–230° C.

19. The process of claim 10 wherein said reaction temperature is from 185° C.–230° C.

20. The process of claim 13 wherein said reaction temperature is from 185° C.–230° C.

* * * * *

UNITED STATES PATENT AND TRADEMARK OFFICE
CERTIFICATE OF CORRECTION

PATENT NO. : 4,851,565
DATED      : July 25, 1989
INVENTOR(S): FRANZ MERGER et al It is certified that error appears in the above-identified patent and that said Letters Patent is hereby corrected as shown below:

On first page of patent for bibliographic data,

ICI/REPAT Code 30 Foreign Application Priority

Data: add April 30, 1979 (DE) Fed.Rep. of Germany -

2917493.

Signed and Sealed this

Seventeenth Day of July, 1990

Attest:

HARRY F. MANBECK, JR.

*Attesting Officer*    *Commissioner of Patents and Trademarks*